United States Patent
Molina et al.

(10) Patent No.: US 11,497,883 B2
(45) Date of Patent: Nov. 15, 2022

(54) SYSTEM AND METHOD FOR ENHANCING REM SLEEP WITH SENSORY STIMULATION

(71) Applicant: KONINKLIJKE PHILIPS N.V., Eindhoven (NL)

(72) Inventors: Gary Nelson Garcia Molina, Madison, WI (US); Noah Papas, Murrysville, PA (US); Jesse Salazar, Gibsonia, PA (US); Bhavdeep Singh Biring, Export, PA (US); Michele Bellesi, Eindhoven (NL); David Pollard White, Denver, CO (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 187 days.

(21) Appl. No.: 16/724,536

(22) Filed: Dec. 23, 2019

(65) Prior Publication Data
US 2020/0197656 A1    Jun. 25, 2020

Related U.S. Application Data

(60) Provisional application No. 62/784,584, filed on Dec. 24, 2018.

(51) Int. Cl.
*A61M 21/00*    (2006.01)
*G06N 3/02*    (2006.01)

(52) U.S. Cl.
CPC .............. *A61M 21/00* (2013.01); *G06N 3/02* (2013.01); *A61M 2021/0027* (2013.01);
(Continued)

(58) Field of Classification Search
CPC .......... A61M 21/00; A61M 2021/0027; A61M 2230/04; A61M 2230/10; A61M 2230/18;
(Continued)

(56) References Cited

U.S. PATENT DOCUMENTS

| | | | | |
|---|---|---|---|---|
| 5,280,791 A | * | 1/1994 | Lavie | A61B 5/352 600/509 |
| 6,669,627 B1 | * | 12/2003 | Campbell | A61N 5/0618 600/27 |

(Continued)

FOREIGN PATENT DOCUMENTS

WO    2017115368 A1    7/2017

OTHER PUBLICATIONS

Elsenbruch, S., Harnish, M.J. & Orr, W.C., 1999. Heart rate variability during waking and sleep in healthy males and females. Sleep, 22(8), pp. 1067-1071. Available at: http://www.ncbi.nlm.nih.gov/pubmed/10617167.
(Continued)

*Primary Examiner* — Sunita Reddy

(57) ABSTRACT

The present disclosure pertains to a system and method for automatically detecting rapid eye movement (REM) sleep and delivering sensory stimulation to prolong REM duration, without disturbing sleep. The sensory stimulation may be auditory or other stimulation. The system and method ensure timely delivery of the stimulation and automatically adjust the amount, intensity, and/or timing of stimulation as necessary. REM sleep is detected based on brain activity, cardiac activity and/or other information. REM sleep may be detected and/or predicted by a trained neural network. The amount, timing, and/or intensity of the sensory stimulation may be determined and/or modulated to enhance REM sleep in a subject based on one or more values of one or more intermediate layers of the neural network and one or more brain activity and/or cardiac activity parameters.

13 Claims, 5 Drawing Sheets

(52) U.S. Cl.
 CPC ..... *A61M 2230/04* (2013.01); *A61M 2230/10* (2013.01); *A61M 2230/18* (2013.01)

(58) Field of Classification Search
 CPC .. A61M 2021/0016; A61M 2021/0022; A61M 2021/0044; A61M 2021/0072; A61M 2205/18; A61M 2205/3375; A61M 2205/505; A61M 2205/507; A61M 2230/30; A61M 2230/42; A61M 2230/50; A61M 21/02; G06N 3/02; G06N 3/0454; G06N 3/084; A61B 5/369; A61B 5/4812; A61B 5/7267; G16H 20/30; G16H 50/20
 USPC ...................................... 600/26–28
 See application file for complete search history.

(56) References Cited

U.S. PATENT DOCUMENTS

| | | | | |
|---|---|---|---|---|
| 2006/0293608 | A1* | 12/2006 | Rothman | A61B 5/369 600/545 |
| 2011/0015469 | A1* | 1/2011 | Walter | A61M 21/00 600/27 |
| 2011/0137188 | A1* | 6/2011 | Kuo | A61B 5/4809 600/509 |
| 2011/0295083 | A1* | 12/2011 | Doelling | A61B 5/11 600/301 |
| 2016/0082222 | A1* | 3/2016 | Garcia Molina | A61B 5/375 600/27 |
| 2017/0252534 | A1* | 9/2017 | Nofzinger | A61H 9/0007 |
| 2017/0340854 | A1* | 11/2017 | Geerlings | A61B 5/4836 |
| 2019/0001117 | A1* | 1/2019 | Ben-David | A61B 5/4836 |

OTHER PUBLICATIONS

Iber, C. et al., 2007. The AASM Manual for the Scoring of Sleep and Associated Events: Rules, Terminology and Technical Specifications First., American Academy of Sleep Medicine.
Della Monica, C. et al., 2018. Rapid Eye Movement Sleep, Sleep Continuity and Slow Wave Sleep as Predictors of Cognition, Mood, and Subjective Sleep Quality in Healthy Men and Women, Aged 20-84 Years. Frontiers in Psychiatry, Jun. 9, p. 255.
Mouze-Amady, M., Sockeel, P. & Leconte, P., 1986. Modification of REM sleep behavior by REMs contingent auditory stimulation in man. Physiology & Behavior, 37(4), pp. 543-548.
Pase, M.P. et al., 2017. Sleep architecture and the risk of incident dementia in the community. Neurology, 89, pp. 1244-1250. Available at: http://www.neurology.org/lookup/doi/10.1212/WNL.0000000000005047.
Salin-Pascual, R.J. et al., 1991. Effects of auditory stimulation during rapid eye movement sleep in healthy volunteers and depressed patients. Psychiatry research, 38(3), pp. 237-246.
Shrivastava, D. et al., 2014. How to interpret the results of a sleep study. Journal of Community Hospital Internal Medicine Perspectives, 4(5), p. 24983.
Song, Y. et al., 2015. Relationships Between Sleep Stages and Changes in Cognitive Function in Older Men: The MrOS Sleep Study. Sleep, 38(3), pp. 411-421.
Zhang, L. et al., 2016. Effect of low-intensity pure tone auditory stimulation on patients with rapid eye movement sleep behavior disorder. Neurological Research, 38(9), pp. 792-798.
International Search Report and Written Opinion, International Application No. PCT/EP2019/086753, dated Feb. 28, 2020.
Ngo, H. et al., "Auditory Closed-Loop Stimulation of the Sleep Slow Oscillation Enhances Memory", Neuron, vol. 78, No. 3, May 2013.
Lim, A. et al., "Selective enhancement of rapid eye movement sleep by deep brain stimulation of the human pons", Annals of Neurologym vol. 66, No. 1, Jul. 2009.

* cited by examiner

SYSTEM AND METHOD FOR ENHANCING REM SLEEP WITH SENSORY STIMULATION

CROSS-REFERENCE TO PRIOR APPLICATIONS

This application claims the benefit of U.S. Provisional Application No. 62/784,584, filed on 24 Dec. 2018. This application is hereby incorporated by reference herein.

BACKGROUND

1. Field

The present disclosure pertains to a system and method for enhancing rapid eye movement (REM) sleep by delivering sensory stimulation to a subject during a sleep session.

2. Description of the Related Art

Systems for monitoring sleep and delivering sensory stimulation to subjects during sleep are known. Electroencephalogram (EEG) sensor based sleep monitoring and sensory stimulation systems are known. These systems are state-based, meaning stimulation is delivered responsive to EEG parameters breaching sleep stage stimulation delivery thresholds. The sleep state stimulation delivery thresholds typically indicate deep sleep (e.g., NREM Stage N2 or N3 sleep). These systems do not deliver stimulation to enhance REM sleep. As a result, advantages of enhanced REM sleep are not experience by users of typical systems.

SUMMARY

It would be advantageous to enhance rapid eye movement (REM) sleep by delivering sensory stimulation to a subject during a sleep session automatically with a closed loop system.

Accordingly, one or more aspects of the present disclosure relate to a system configured to enhance REM sleep by delivering sensory stimulation to a subject during a sleep session. The system comprises one or more sensors, one or more sensory stimulators, one or more hardware processors, and/or other components. The one or more sensors are configured to generate output signals conveying information related to sleep stages of the subject during the sleep session. The one or more sensory stimulators are configured to provide the sensory stimulation to the subject during the sleep session. The one or more hardware processors are coupled to the one or more sensors and the one or more sensory stimulators. The one or more hardware processors are configured by machine-readable instructions. The one or more hardware processors are configured to detect REM sleep in the subject during the sleep session based on the output signals. The one or more hardware processors are configured to control the one or more sensory stimulators to provide the sensory stimulation to the subject during the REM sleep to enhance the REM sleep in the subject during the sleep session.

In some embodiments, the one or more sensors are configured such that the information related to the sleep stages of the subject comprises information related to brain activity and/or cardiac activity in the subject. In some embodiments, the one or more sensors comprise one or more electroencephalogram (EEG) electrodes configured to generate the information related to brain activity, one or more electrocardiogram (ECG) sensors configured to generate the information related to cardiac activity, one or more photoplethysmography (PPG) sensors configured to generate the information related to cardiac activity, and/or other sensors.

In some embodiments, the one or more sensors are configured such that the information related to the sleep stages of the subject comprises the information related to cardiac activity. In some embodiments, the one or more hardware processors are configured to detect REM sleep in the subject responsive to a ratio between a low frequency component of the information related to cardiac activity and a high frequency component of the information related to cardiac activity breaching a ratio threshold.

In some embodiments, the one or more hardware processors are further configured to detect REM sleep in the subject responsive to determining that the subject has remained in REM sleep for a continuous threshold amount of time during the sleep session.

In some embodiments, the one or more hardware processors are configured such that detecting REM sleep in the subject comprises obtaining historical sleep stage information for the subject and/or a population of subjects demographically similar to the subject. The historical sleep stage information is related to brain activity and/or cardiac activity of the subject and/or the population of subjects that indicates sleep stages over time during sleep sessions of the subject and/or the population of subjects. Detecting REM sleep includes causing a neural network to be trained based on the historical sleep stage information by providing the historical sleep stage information as input to the neural network; and causing, based on the output signals, the trained neural network to: (1) determine periods when the subject is experiencing REM sleep during the sleep session; or (2) predict future times during the sleep session at which the subject will experience REM sleep. The trained neural network comprises an input layer, an output layer, and one or more intermediate layers between the input layer and the output layer.

In some embodiments, the one or more hardware processors are configured such that controlling the one or more sensory stimulators to provide the sensory stimulation to the subject during the REM sleep to enhance the REM sleep in the subject during the sleep session comprises: determining, with respect to (1) the periods when the subject is experiencing REM sleep, or (2) each of the future times, one or more values generated by the one or more intermediate layers of the trained neural network. Controlling the one or more sensory stimulators comprises causing the one or more sensory stimulators to provide the sensory stimulation to the subject (1) during the periods when the subject is experiencing REM sleep, or (2) at the future times. Controlling the one or more sensory stimulators comprises determining, and/or causing the one or more sensory stimulators to modulate, an amount, a timing, and/or an intensity of the sensory stimulation provided to the subject based on the one or more values of the one or more intermediate layers.

In some embodiments, the one or more hardware processors are configured to determine one or more brain activity and/or cardiac activity parameters of the subject based on the output signals. The one or more brain activity and/or cardiac activity parameters are indicative of the sleep stages of the subject. The one or more hardware processors are configured to determine, and/or cause the one or more sensory stimulators to modulate, the amount, timing, and/or intensity of the sensory stimulation to enhance REM sleep in the subject based on the one or more values of the one or more intermediate layers and the one or more brain activity and/or cardiac activity parameters.

In some embodiments, the one or more hardware processors are configured such that the one or more values from the one or more intermediate layers of the trained neural network include values from one or more convolutional layers and values from one or more recurrent layers of the trained neural network. The one or more hardware processors are configured to determine, and/or cause the one or more sensory stimulators to modulate, the amount, timing, and/or intensity of the sensory stimulation based on the one or more brain activity and/or cardiac activity parameters, the values from the one or more convolutional layers, and the values from the one or more recurrent layers.

In some embodiments, the one or more sensory stimulators are configured such that the sensory stimulation comprises audible tones. The one or more hardware processors are configured such that controlling the one or more sensory stimulators to provide the sensory stimulation to the subject during the REM sleep to enhance the REM sleep in the subject during the sleep session comprises: determining the amount, timing, and/or intensity of the sensory stimulation by determining an inter tone interval, a tone volume, and/or a tone frequency; and/or causing the one or more sensory stimulators to modulate the amount, timing, and/or intensity of the sensory stimulation. The modulation comprises adjusting the inter tone interval, the tone volume, and/or the tone frequency, responsive to an indication the subject is experiencing one or more micro-arousals.

In some embodiments, the stimulation is timed to synchronize to the detection of a Ponto-geniculo-occipital (PGO) wave in the EEG.

Another aspect of the present disclosure relates to a method for enhancing REM sleep by delivering sensory stimulation to a subject during a sleep session with an enhancement system. The system comprises one or more sensors, one or more sensory stimulators, one or more hardware processors, and/or other components. The method comprises: generating, with the one or more sensors, output signals conveying information related to sleep stages of the subject during the sleep session; detecting, with the one or more hardware processors, REM sleep in the subject during the sleep session based on the output signals, and controlling, with the one or more hardware processors, the one or more sensory stimulators to provide the sensory stimulation to the subject during the REM sleep to enhance the REM sleep in the subject during the sleep session.

In some embodiments, the information related to the sleep stages of the subject comprises information related to brain activity and/or cardiac activity in the subject. In some embodiments, the information related to the sleep stages of the subject comprises the information related to cardiac activity, and the one or more hardware processors are configured to detect REM sleep in the subject responsive to a ratio between a low frequency component of the information related to cardiac activity and a high frequency component of the information related to cardiac activity breaching a ratio threshold.

In some embodiments, detecting REM sleep in the subject comprises obtaining historical sleep stage information for the subject and/or a population of subjects demographically similar to the subject. The historical sleep stage information is related to brain activity and/or cardiac activity of the subject and/or the population of subjects that indicates sleep stages over time during sleep sessions of the subject and/or the population of subjects. Detecting REM sleep in the subject comprises causing a neural network to be trained based on the historical sleep stage information by providing the historical sleep stage information as input to the neural network; and causing, based on the output signals, the trained neural network to: (1) determine periods when the subject is experiencing REM sleep during the sleep session; or (2) predict future times during the sleep session at which the subject will experience REM sleep. The trained neural network comprises an input layer, an output layer, and one or more intermediate layers between the input layer and the output layer. Controlling the one or more sensory stimulators to provide the sensory stimulation to the subject during the REM sleep to enhance the REM sleep in the subject during the sleep session comprises determining, with respect to (1) the periods when the subject is experiencing REM sleep, or (2) each of the future times, one or more values generated by the one or more intermediate layers of the trained neural network; causing the one or more sensory stimulators to provide the sensory stimulation to the subject (1) during the periods when the subject is experiencing REM sleep, or (2) at the future times, and determining, and/or causing the one or more sensory stimulators to modulate, an amount, a timing, and/or an intensity of the sensory stimulation provided to the subject based on the one or more values of the one or more intermediate layers.

In some embodiments, the method further comprises determining, with the one or more hardware processors, one or more brain activity and/or cardiac activity parameters of the subject based on the output signals. The one or more brain activity and/or cardiac activity parameters are indicative of the sleep stages of the subject. In some embodiments, the method further comprises determining, and/or causing the one or more sensory stimulators to modulate, with the one or more hardware processors, the amount, timing, and/or intensity of the sensory stimulation to enhance REM sleep in the subject based on the one or more values of the one or more intermediate layers and the one or more brain activity and/or cardiac activity parameters.

In some embodiments, the stimulation is timed to synchronize to the detection of a Ponto-geniculo-occipital (PGO) wave in the EEG.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
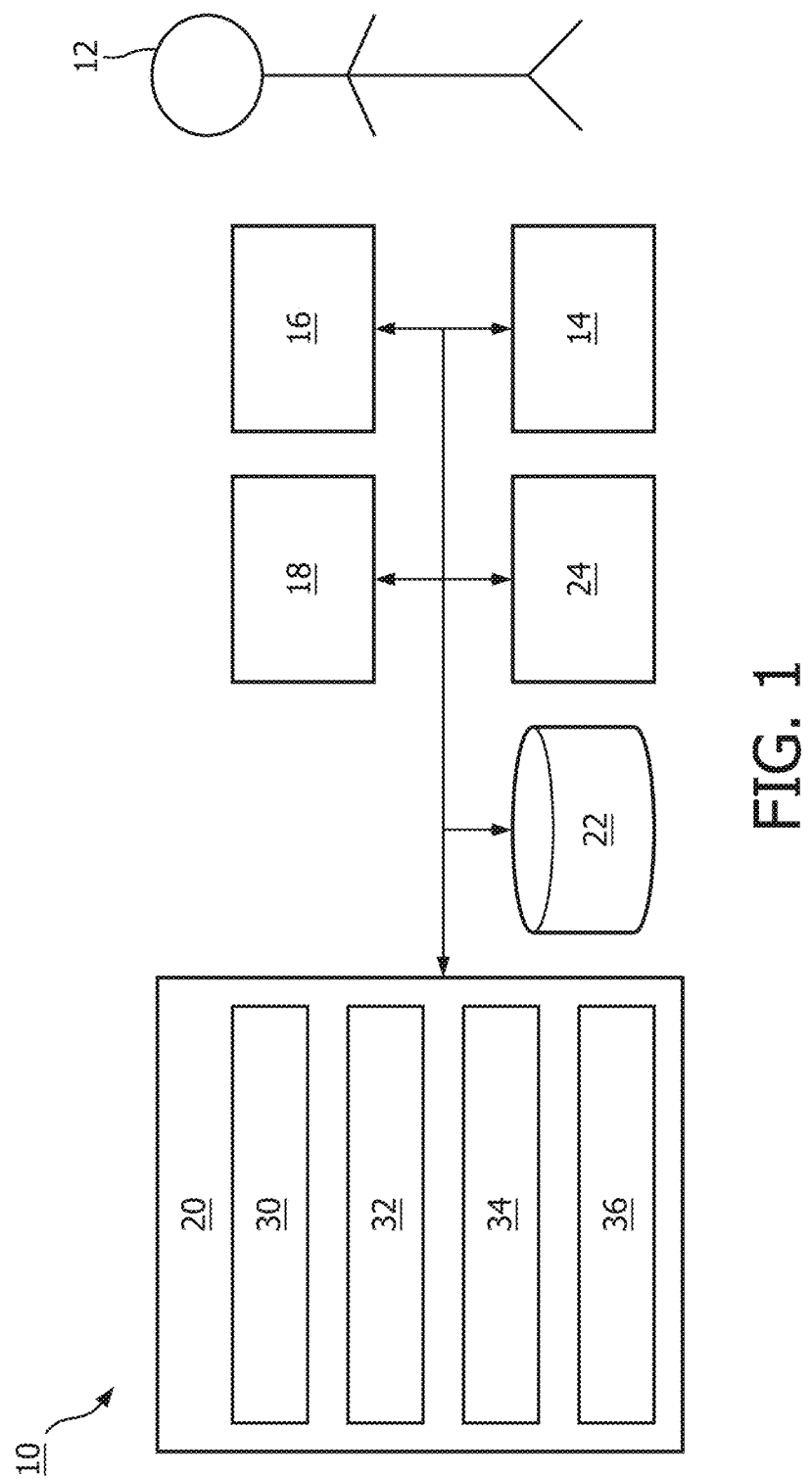
FIG. 1 is a schematic illustration of a system configured to enhance REM sleep by delivering sensory stimulation to a subject during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a subject 12 during a sleep session. System 10 is configured to facilitate delivery of sensory stimulation to subject 12 to enhance the restorative effects of sleep in subject 12 and/or for other purposes. System 10 is configured such that sensory stimulation including auditory and/or other stimulation delivered during sleep enhances rapid eye movement (REM) sleep in subject 12 without causing arousals. As described herein, in some embodiments, system 10 is configured to determine periods of REM sleep during a sleep session (e.g., based on output from a neural network and/or other information, based on cardiac activity, and/or based on other information). In some embodiments, based on such determinations, system 10 is configured to modulate sensory (e.g., auditory) stimulation delivered to subject 12 to enhance REM sleep without causing arousals. In some embodiments, periods of REM sleep may be determined in real-time and/or near real-time during a sleep session of subject 12.

REM sleep is an important component of sleep quality and enhanced REM sleep correlates with enhanced performance accuracy (e.g., in tasks performed by a subject after a sleep session). More REM sleep, and not necessarily slow wave sleep, is associated with less cognitive decline in subjects over time. Sensory stimulation (e.g., auditory tones) delivered during REM sleep may prolong REM duration during sleep sessions. Prior attempts to enhance REM sleep in subjects have required the close supervision of a sleep expert. The sleep expert monitored polysomnographic signals from subjects during their sleep to detect periods of REM sleep and then manually delivered auditory stimulation to the subjects. In addition to the disadvantage of requiring the intervention of a sleep expert, the manual delivery of sensory stimulation was not accurately or consistently controlled.

System 10 is configured to automatically detect REM sleep and deliver sensory (e.g., auditory) stimulation to subject 12 to prolong REM duration, while substantially preventing sleep disturbance. System 10 ensures timely delivery of the stimulation and automatically adjusts the amount and/or other characteristics (e.g., intensity, timing, etc.) of stimulation. System 10 addresses the limitations of prior art systems (e.g., requiring manual input from a sleep expert, inaccurate or inconsistent delivery of sensory stimulation by the sleep expert, etc.) by leveraging machine-learning models (e.g., deep neural networks and/or any other supervised machine learning algorithm as described below) for automatic, real-time or near real-time, closed loop, sensor output signal based enhancement of REM sleep by delivering sensory stimulation to subject 12 during a sleep session. System 10 uses the overall output from the machine-learning models for sleep staging, as well as intermediate values output from the models to modulate (e.g., the amount of) sensory stimulation provided by system 10. In some embodiments, system 10 does not use machine-learning models, and instead detects REM sleep based on cardiac activity thresholds and/or other thresholds for subject 12. It should be noted that system 10 is described herein as configured to enhance REM sleep (e.g., configured to increase the percent of REM sleep). This may include characterization of a duration and/or percent of eye movements (or phasic activity) during REM, for example, and/or other characterization. In some embodiments, system 10 includes one or more of a sensor 14, a sensory stimulator 16, external resources 18, a processor 20, electronic storage 22, a user interface 24, and/or other components.

Sensor 14 is configured to generate output signals conveying information related to sleep stages of subject 12 during a sleep session. The output signals conveying information related to sleep stages of subject 12 may include information related to brain activity in subject 12, cardiac activity in subject 12, and/or other physiological activity in subject 12. As such, sensor 14 is configured to generate output signals conveying information related to brain activity, cardiac activity, and/or other activity in subject 12. In some embodiments, sensor 14 is configured to generate output signals conveying information related to stimulation provided to subject 12 during sleep sessions. In some embodiments, the information in the output signals from sensor 14 is used to control sensory stimulator 16 to provide sensory stimulation to subject 12 (as described below).

Sensor 14 may comprise one or more sensors that generate output signals that convey information related to brain activity in subject 12 directly. For example, sensor 14 may include electroencephalogram (EEG) electrodes configured to detect electrical activity along the scalp of subject 12 resulting from current flows within the brain of subject 12. Sensor 14 may comprise one or more sensors that generate output signals conveying information related to brain activity of subject 12 indirectly. For example, one or more sensors 14 may comprise a heart rate sensor that generates an output based on a heart rate of subject 12 (e.g., sensor 14 may be a heart rate sensor than can be located on the chest of subject 12, and/or be configured as a bracelet on a wrist of subject 12, and/or be located on another limb of subject 12), movement of subject 12 (e.g., sensor 14 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, sensor 14 may comprise one or more of EEG electrodes, an electrooculogram (BOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to subject 12, the brain activity of subject 12, the cardiac activity of subject 12, and/or other sensors. Although sensor 14 is illustrated at a single location near subject 12, this is not intended to be limiting. Sensor 14 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

In FIG. 1, sensor 14, sensory stimulator 16, processor 20, electronic storage 22, and user interface 24 are shown as separate entities. This is not intended to be limiting. Some and/or all of the components of system 10 and/or other components may be grouped into one or more singular devices. For example, these and/or other components may be included in a headset and/or other garments worn by subject 12. Such a headset may include, for example, sensing electrodes, a reference electrode, one or more devices associated with an EEG, means to deliver auditory stimulation (e.g., a wired and/or wireless audio device and/or other devices), and one or more audio speakers. In this example, the audio speakers may be located in and/or near the ears of subject 12 and/or in other locations. The reference electrode may be located behind the ear of subject 12, and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to subject 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, user interface 24, and/or other components of system 10 shown in FIG. 1.

Stimulator 16 is configured to provide sensory stimulation to subject 12. Sensory stimulator 16 is configured to provide auditory, visual, somatosensory, electric, magnetic, and/or sensory stimulation to subject 12 prior to a sleep session, during a sleep session, and/or at other times. In some embodiments, a sleep session may comprise any period of time when subject 12 is sleeping and/or attempting to sleep. Sleep sessions may include nights of sleep, naps, and/or other sleeps sessions. For example, sensory stimulator 16 may be configured to provide stimuli to subject 12 during a sleep session to enhance REM sleep in subject 12, and/or for other purposes.

Sensory stimulator 16 is configured to enhance REM sleep in subject 12 through non-invasive brain stimulation and/or other methods. Sensory stimulator 16 may be configured to enhance REM sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, acoustic tones may be provided to subject 12 to enhance REM sleep in subject 12. The acoustic tones may include one or more series of tones of a determined length separated from each other by an inter-tone interval. The volume (e.g., the intensity) of individual tones may be modulated based on various factors (as described herein). The length of individual tones (e.g., the timing) and/or the inter tone interval (e.g., the timing) may also be adjusted. The pitch and tone may also be adjusted. In some embodiments, this example auditory stimulation is in the form of 40-millisecond long pink-noise tones (the pink noise frequency limits are 500 Hz to 5 KHz). The inter-tone interval may be 10 seconds, and the volume of the stimulation may be 80 dB. This example is not intended to be limiting. Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. For example, external resources 18 may include sources of historical sleep stage information for subject 12, historical sleep stage information for a population of subjects demographically similar to subject 12, and/or other information. The historical sleep stage information for subject 12 and/or the population of subjects may be related to brain activity and/or cardiac activity of subject 12 and/or the population of subjects that indicates sleep stage over time during sleep sessions of subject 12 and/or the population of subjects. In some embodiments, the historical sleep stage information for subject 12 and/or the population of subjects may be related to a user population in a given geographical area; demographic information related to gender, ethnicity, age, a general health level, and/or other demographic information; physiological information (e.g., weight, blood pressure, pulse, etc.) about the population of subjects, and/or other information. In some embodiments, this information may indicate whether an individual user in the population of subjects is demographically, physiologically, and/or otherwise similar to subject 12.

In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 18 may be provided by resources included in system 10. External resources 18 may be configured to communicate with processor 20, user interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity and/or cardiac activity parameters of subject 12, and/or other information. The brain activity and/or cardiac activity parameters are determined based on the output signals from sensor 14 and/or other information. The brain activity and/or cardiac activity parameters indicate depth of sleep in subject 12. In some embodiments, the information in the output signals related to brain activity and/or cardiac activity indicates sleep depth over time. In some embodiments, the information indicating sleep depth over time is or includes information related to REM sleep in subject 12.

In some embodiments, the information indicating sleep depth over time may be indicative of other sleep stages of subject 12. For example, the sleep stages of subject 12 may be associated with REM sleep, non-rapid eye movement (NREM) sleep, and/or other sleep. NREM sleep may be one or more of NREM stage N1, stage N2, or stage N3, and/or other sleep stages. In some embodiments, the sleep stages of subject 12 may be one or more of stage S1, S2, S3, or S4. In some embodiments, NREM stage 2 and/or 3 (and/or S3 and/or S4) may be slow wave (e.g., deep) sleep. In some embodiments, the information that indicates sleep depth over time is and/or is related to one or more additional brain activity and/or cardiac activity parameters.

In some embodiments, the information related to brain activity and/or cardiac activity that indicates sleep depth over time is and/or includes EEG information, ECG information, PPG information, and/or other information generated during sleep sessions of subject 12 and/or at other times. In some embodiments, brain activity and/or cardiac activity parameters may be determined based on the EEG information, the ECG information, the PPG information, and/or other information. In some embodiments, the brain activity and/or cardiac activity parameters may be determined by information component 30 and/or other components of system 10. In some embodiments, the brain activity and/or cardiac activity parameters may be previously determined and be part of the historical sleep stage information obtained from external resources 18 (described below). In some embodiments, the one or more brain activity parameters are and/or are related to a frequency, amplitude, phase, presence of specific sleep patterns such as eye movements, ponto-geniculo-occipital (PGO) wave, slow wave, and/or other characteristics of an EEG signal. In some embodiments, the one or more brain activity parameters are determined based on the frequency, amplitude, and/or other characteristics of the EEG signal. In some embodiments, the one or more cardiac activity parameters are and/or are related to a frequency, amplitude, phase, heart rate, heart rate variability, inter beat intervals, power in a low frequency band (0.05 to 0.15 Hz), power in a high frequency band (0.15 to 0.4 Hz), and/or other characteristics of an ECG and/or a PPG signal. In some embodiments, the one or more brain activity and/or cardiac activity parameters are determined based on the frequency, amplitude, and/or other characteristics of the EEG, ECG, and/or PPG signal. In some embodiments, the determined brain activity and/or cardiac activity parameters and/or the characteristics of the EEG, ECG, and/or PPG may be and/or indicate sleep stages that correspond to the REM and/or NREM sleep stages described above.

Information component 30 is configured to obtain historical sleep stage information. In some embodiments, the historical sleep stage information is for subject 12, a population of subjects demographically similar to subject 12, and/or other users. In some embodiments, the population of subjects is demographically similar to subject 12. In some embodiments, the historical sleep stage information is for subject 12. The historical sleep stage information is related to brain activity, cardiac activity, and/or other physiological of the population of subjects and/or subject 12 that indicates sleep stages over time during previous sleep sessions of the population of subjects and/or subject 12. The historical sleep stage information is related to sleep stages and/or other brain and/or cardiac activity parameters of the population of subjects and/or subject 12 during corresponding sleep sessions, and/or other information.

In some embodiments, information component 30 is configured to obtain the historical sleep stage information electronically from external resources 18, electronic storage 22, and/or other sources of information. In some embodiments, obtaining the historical sleep stage information electronically from external resources 18, electronic storage 22, and/or other sources of information comprises querying one more databases and/or servers; uploading information and/or downloading information, facilitating user input (e.g., criteria used to define a target patient population input via user interface 24), sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep stage information (e.g., length of sleep sessions, number of sleep sessions, etc.) and/or perform other operations.

Model component 32 is configured to cause a machine-learning model to be trained using the historical sleep stage information. In some embodiments, the machine-learning model is trained based on the historical sleep stage information by providing the historical sleep stage information as input to the machine-learning model. In some embodiments, the machine-learning model may be and/or include mathematical equations, algorithms, plots, charts, networks (e.g., neural networks), and/or other tools and machine-learning model components. For example, the machine-learning model may be and/or include one or more neural networks having an input layer, an output layer, and one or more intermediate or hidden layers and/or any other supervised machine learning algorithms. In some embodiments, the one or more neural networks and/or any other supervised machine learning algorithms may be and/or include deep neural networks (e.g., neural networks that have one or more intermediate or hidden layers between the input and output layers).

As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

As described above, a trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. The detected and/or predicted sleep stages and/or future times of REM sleep are generated based on the information in the output signals from sensor 14 as processed by the layers of the neural network.

Model component 32 is configured such that the trained neural network and/or any other supervised machine learning algorithms are caused to detect and/or predict REM sleep in subject 12. In some embodiments, this may be and/or include (1) determining periods when subject 12 is experiencing REM sleep during the sleep session; (2) predicting future times during the sleep session at which subject 12 will experience REM sleep, and/or other operations. In some embodiments, this includes causing the trained neural network and/or any other supervised machine learning algorithms to predict future times during the sleep session at which subject 12 will be in REM sleep. The determined and/or predicted REM sleep, and/or timing, indicates whether subject 12 is (or will be) in REM sleep for stimulation and/or other information. By way of a non-limiting example, a trained neural network may be caused to indicate predicted sleep stages and/or future times and/or timing of the deep sleep stages for the user based on the output signals (e.g., using the information in the output signals as input for the model) and/or other information. The trained neural network is configured to indicate sleep stages predicted to occur at future times for subject 12 during the sleep session. In some embodiments, model component 32 is configured to provide the information in the output signals to the neural network in temporal sets that correspond to individual periods during the sleep session. In some embodiments, model component 32 is configured to cause the trained neural network to output the determined and/or predicted sleep stages and/or predicted times of REM sleep for subject 12 during the sleep session based on the temporal sets of information. (The functionality of model component 32 is further discussed below relative to FIGS. 2-3.)

Control component 34 is configured to control stimulator 16 to provide stimulation to subject 12 during sleep and/or at other times. Control component 34 is configured to cause sensory stimulator 16 to provide the sensory stimulation to subject 12 during REM sleep to enhance REM sleep in subject 12 during a sleep session. Control component 34 is configured to cause sensory stimulator 16 to provide sensory stimulation to subject 12 based on detected REM sleep and/or a predicted REM sleep stage (e.g., the output from model component 32) and/or future times at which subject 12 will be in REM sleep, and/or other information. Control component 34 is configured to cause sensory stimulator 16 to provide the sensory stimulation to subject 12 based on the detected and/or predicted REM sleep stage, and/or future times subject 12 will be in REM sleep, and/or other information over time during the sleep session. Control component 34 is configured to cause sensory stimulator 16 to provide sensory stimulation to subject 12 responsive to subject 12 being in, or likely being in, REM sleep for stimulation. For example, control component 34 is configured such that controlling one or more sensory stimulators 16 to provide the sensory stimulation to subject 12 during the REM sleep to enhance the REM sleep in subject 12 during the sleep session comprises: determining, with respect to (1) the periods when subject 12 is experiencing REM sleep, or (2) each of the future times, one or more values generated by the one or more intermediate layers of the trained neural network; causing one or more sensory stimulators 16 to provide the sensory stimulation to subject 12 (1) during the periods when subject 12 is experiencing REM sleep, or (2) at the future times, and determining, and/or causing one or more sensory stimulators 16 to modulate (e.g., as described herein), an amount, a timing, and/or intensity of the sensory stimulation provided to subject 12 based on the one or more values of the one or more intermediate layers. In some embodiments, stimulators 16 are controlled by control component 34 to enhance REM sleep through (e.g. peripheral auditory, magnetic, electrical, and/or other) stimulation delivered during REM sleep (as described herein).

In some embodiments, control component 34 is configured to control sensory stimulator 16 to deliver sensory stimulation to subject 12 responsive to model component 32 determining that subject 12 has remained in REM sleep for a continuous threshold amount of time during the sleep session. For example, model component 32 and/or control component 34 may be configured such that on detection (or prediction) of REM sleep, model component 32 starts a (physical or virtual) timer configured to track the time subject 12 spends in REM sleep. Control component 34 is configured to deliver auditory stimulation responsive to the duration that subject 12 spends in continuous REM sleep breaching a predefined duration threshold. In some embodiments, the predefined duration threshold is determined at manufacture of system 10 and/or at other times. In some embodiments, the predefined duration threshold is determined based on information from previous sleep sessions of subject 12 and/or subjects demographically similar to subject 12 (e.g., as described above). In some embodiments, the predefined duration threshold is adjustable via user interface 24 and/or other adjustment mechanisms.

In some embodiments, the predefined REM sleep duration threshold may be one minute and/or other durations, for example. By way of a non-limiting example, control component 34 may be configured such that auditory stimulation starts once a minute of continuous REM sleep in subject 12 is detected (and/or predicted). The auditory stimulation may be in the form of 40-millisecond long pink-noise tones (500 Hz to 5 KHz), with an inter-tone interval of 10 seconds, and a volume of 80 dB. In some embodiments, control component 34 is configured to control sensory stimulator 16 to hold these parameters of the stimulation constant for as long as non-tone related sleep micro-arousals are detected. On detection of sleep stage transitions (e.g., from REM to some other sleep stage), however, control component 34 is configured to stop stimulation.

Modulation component 36 is configured to cause sensory stimulator 16 to modulate an amount, a timing, and/or intensity of the sensory stimulation. Modulation component 36 is configured to cause sensory stimulator 16 to modulate the amount, timing, and/or intensity of the sensory stimulation based on the brain activity parameters, cardiac activity parameters, values output from the intermediate layers of the trained neural network, and/or other information. As an example, sensory stimulator 16 is caused to modulate the timing and/or intensity of the sensory stimulation based on the brain activity parameters, the cardiac activity parameters, the values output from the convolutional layers, the values output from the recurrent layers, and/or other information. For example, modulation component 36 may be configured such that sensory stimulation is delivered with an intensity that is proportional to a predicted probability value (e.g., an output from an intermediate layer of a neural network) of a particular sleep stage (e.g., REM). In this example, the higher the probability of REM sleep, the more likely the stimulation continues. If sleep micro-arousals are detected and the sleep stage remains REM, modulation component 36 may be configured such that the volume is decreased (by for instance five dBs) responsive to individual micro-arousal detections.

Figure 2:
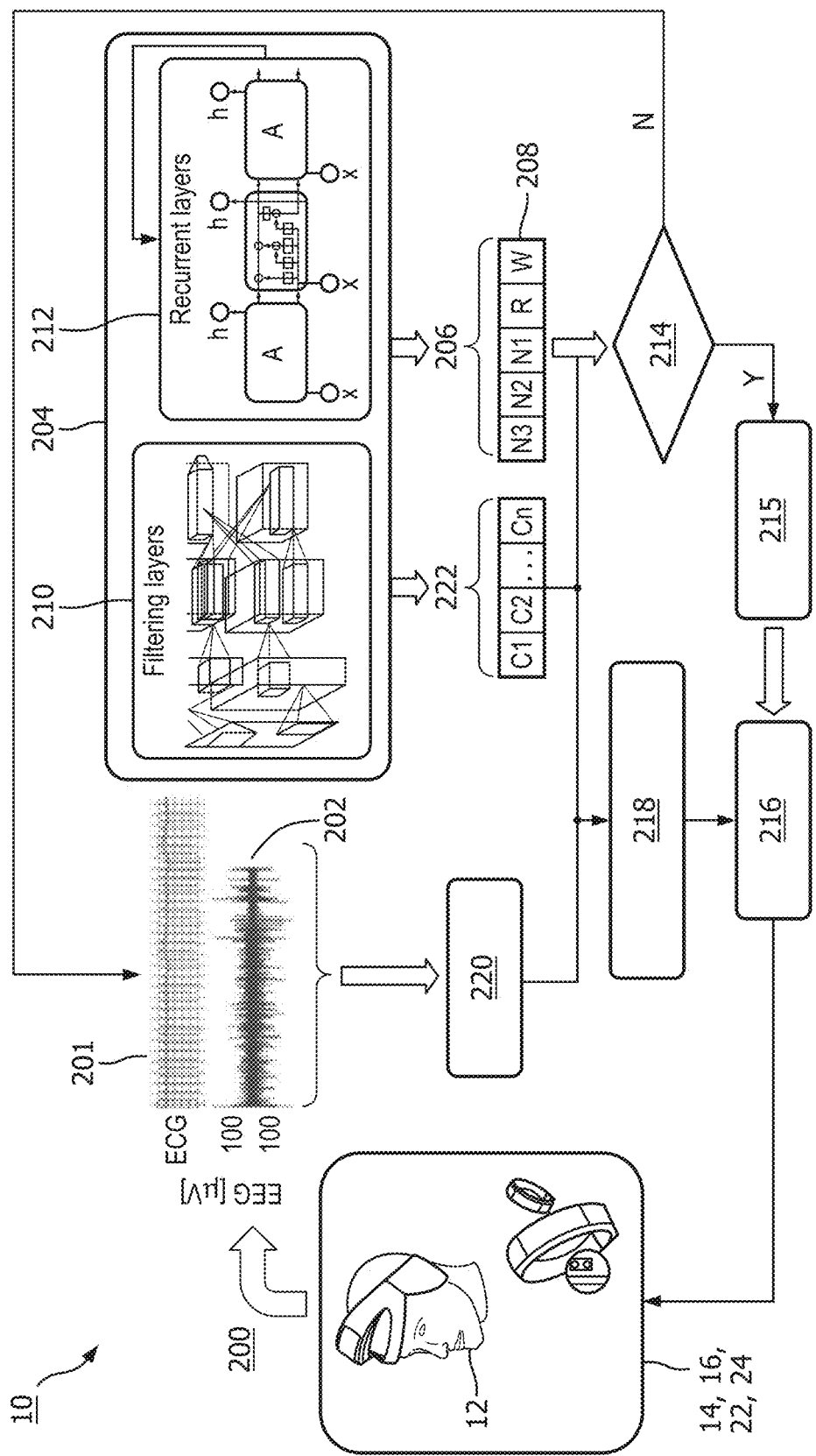
FIG. 2 illustrates several of the operations performed by the system, in accordance with one or more embodiments.

By way of a non-limiting example, FIG. 2 illustrates several of the operations performed by system 10 and described above. In the example shown in FIG. 2, an EEG or ECG signal 200 is processed and/or otherwise provided (e.g., by information component 30 and model component 32 shown in FIG. 1) to a deep neural network 204 in temporal windows 201 (ECG) or 202 (EEG). Deep neural network 204 detects and/or predicts 206 future sleep stages 208 (illustrated as N3, N2, N1, R (REM), and W (wakefulness)) and/or future times where a user will be in REM sleep based on the information in temporal windows 201 or 202. In some embodiments, the prediction window is about tens of seconds to a few minutes, for example. Predicting future sleep stages and/or timing of REM sleep facilitates provision of sensory stimulation to enhance REM sleep because it enables system 10 to either withhold stimulation (if deeper sleep stages are detected and/or predicted) or prepare for stimulation with optimized timing and intensity when REM sleep is detected and/or predicted. The architecture of deep neural network 204 includes convolutional layers 210 (which can be thought of as filters) and recurrent layers 212 (which, as just one example, may be implemented as long-short term memory elements) that endow network 204 with memory to be able to use past predictions to refine prediction accuracy.

As shown in FIG. 2, responsive to sleep stage determinations and/or predictions 208 indicating REM sleep 214, stimulation 216 is provided to subject 12 (e.g., from sensory stimulator 16 controlled by control component 34 shown in FIG. 1). In some embodiments, system 10 is configured to detect REM sleep in subject 12 responsive to determining that subject 12 has remained 215 in REM sleep for a continuous threshold amount of time during the sleep session. The intensity and/or timing of stimulation 216 is modulated 218 (e.g., by modulation module 36) based on brain activity and/or cardiac activity parameters 220 (e.g., extracted features of signal 200 determined by information component 30 shown in FIG. 1), outputs 222 from the convolutional layers of the deep neural network (illustrated as constants $C_1, C_2, \ldots, C_n$), and detected and/or predicted sleep stages 208. As described above, in some embodiments, the sensory stimulation comprises audible tones. In these embodiments, sensory stimulators 16 may modulate the amount, timing, and/or intensity of the sensory stimulation responsive to the brain activity and/or cardiac activity parameters and/or the output from the intermediate layers (e.g., convolutional layers 210 and/or recurrent layers 212) indicating subject 12 is in, and/or is predicted to be in REM sleep for stimulation.

Figure 3:
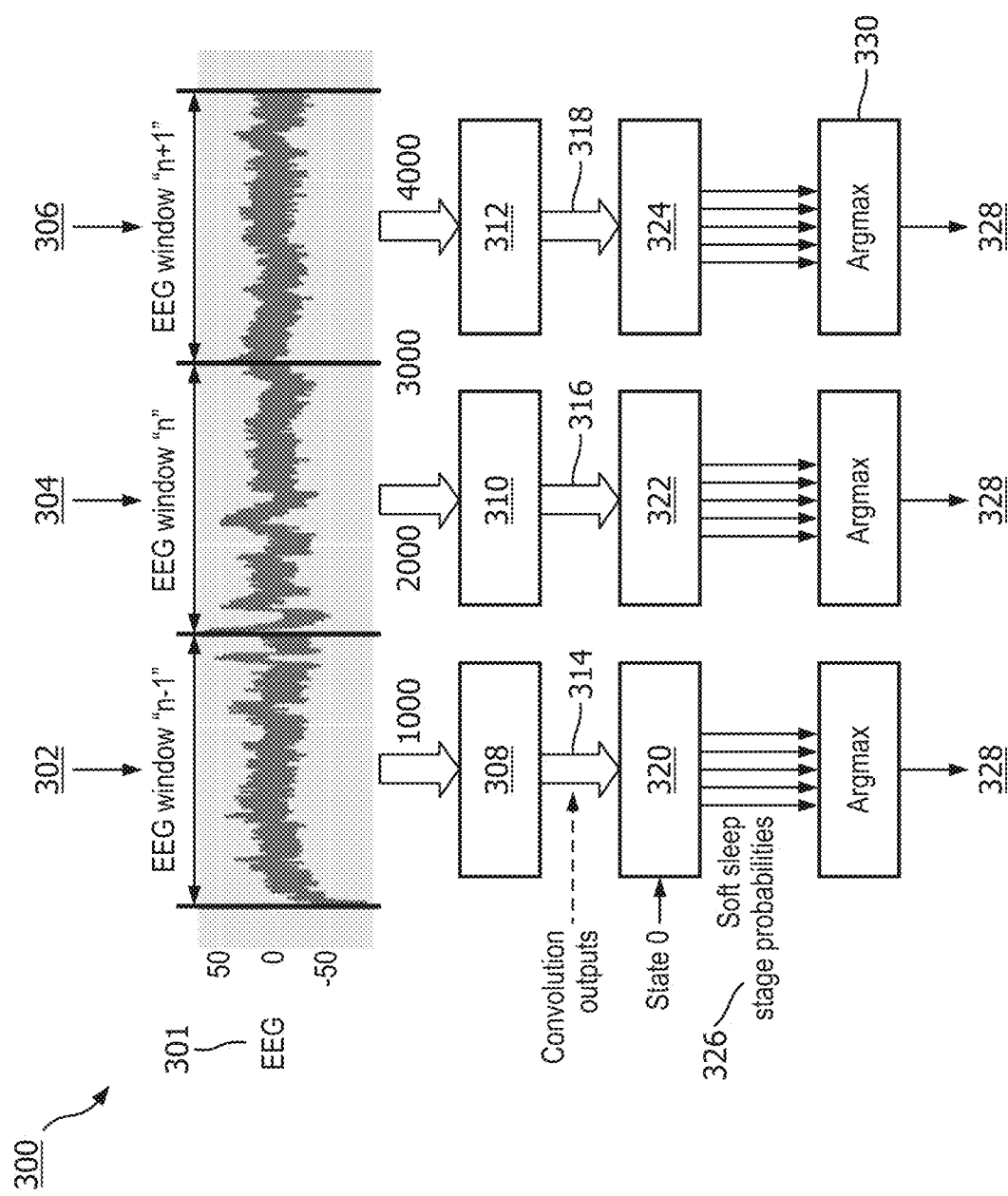
FIG. 3 illustrates example architecture of a deep neural network that is part of the system, in accordance with one or more embodiments.

FIG. 3 illustrates example architecture 300 of a deep neural network (e.g., deep neural network 204 shown in FIG. 2) that is part of system 10 (FIGS. 1 and 2). FIG. 3 illustrates deep neural network architecture 300 for three (unrolled) EEG 301 windows 302, 304, and 306. Architecture 300 includes convolutional layers 308, 310, and 312, and recurrent layers 320, 322, and 324. As described above, convolutional layers 308, 310, and 312 can be thought of as filters and produce convolution outputs 314, 316, and 318 that are fed to recurrent layers 320, 322, 324 (LSTM (long short term memory) layers in this example). The output of architecture 300 for individual windows 302, 304, 306 that are processed are a set of prediction probabilities for individual sleep stages, which are termed "soft output(s)" 326. "Hard" predictions 328 are determined by architecture 300 (model component 32 shown in FIG. 1) by predicting 330 a sleep stage associated with a "soft" output with the highest value (e.g., as described below). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example. "Argmax" in FIG. 3 is an operator that indicates the sleep stage associated with the highest "soft output" (e.g., the highest probability).

For example, a useful property of neural networks is that they can produce probabilities associated with pre-defined sleep stages (e.g. Wake, REM, N1, N2, N3 sleep). Model component 32 (FIG. 1) is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems).

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft-decision) value outputs are available to be used by system 10 to modulate the volume of the stimulation when the deep neural network detects and/or predicts occurrences of REM sleep. In addition, as described herein, parameters determined (e.g., by information component 30 shown in FIG. 1) based on the raw sensor output signals (e.g., EEG, ECG, etc.) can be used to modulate stimulation settings.

As described above, modulation component 36 is configured to cause sensory stimulator 16 to modulate an amount, timing, and/or intensity of the sensory stimulation. Modulation component 36 is configured to cause sensory stimulator to modulate the amount, timing, and/or intensity of the sensory stimulation based on the one or more brain activity, cardiac activity, and/or other parameters, values output from the convolutional and/or recurrent layers of the trained neural network, and/or other information. As an example, the inter tone interval of auditory stimulation provided to subject 12 may be adjusted and/or otherwise controlled (e.g., modulated) based on value outputs from the deep neural network such as convolutional layer value outputs and recurrent layer value outputs (e.g., sleep stage (soft) prediction probabilities). In some embodiments, modulation component 36 is configured to cause one or more sensory stimulators 16 to modulate the amount, timing, and/or intensity of the sensory stimulation, wherein the modulation comprises adjusting the inter tone interval, the tone volume, and/or the tone frequency, responsive to an indication subject 12 is experiencing one or more micro-arousals.

In some embodiments, modulation component 36 is configured to modulate the sensory stimulation based on the brain activity, the cardiac activity, and/or other parameters alone, which may be determined based on the output signals from sensors 14 (e.g., based on a raw EEG signal, ECG signal, etc.). In these embodiments, the output of a deep neural network (and/or other machine learning models) continues to be used to predict sleep stages (e.g., as described above). However, the stimulation intensity and timing is instead modulated based on brain activity, cardiac activity, and/or other parameters or properties determined based on the sensor output signals. In some embodiments, the information in, or determined based on, the sensor output signals can also be combined with intermediate outputs of the network such as output of the convolution layers or the final outputs (soft stages) to modulate intensity and timing (e.g., as described herein).

In some embodiments, system 10 does not use machine-learning models, and instead model component 32 detects REM sleep based on cardiac activity thresholds and/or other thresholds for subject 12. In some embodiments, model component 32 is configured to detect REM sleep in subject 12 responsive to a ratio between a low frequency component of the information related to cardiac activity (e.g., a first cardiac activity parameter) and a high frequency component of the information related to cardiac activity (e.g., a second cardiac activity parameter) breaching a ratio threshold. In such embodiments, sensors 14 may include PPG and ECG sensors embedded in sleep wearable devices configured to generate output signals conveying information used to automatically detect REM sleep by leveraging the fact that spectral properties of heart-beat intervals are distinctly different in REM sleep compared to NREM sleep and wakefulness. For example, let r1, r2, . . . , rQ represent the sequence of inter-beat interval durations in seconds. The Fourier transform of this sequence may be used by model component 32 to determine the spectral heart rate variability as the ratio between the power in the low frequency (LF) band (e.g., 0.05 to 0.15 Hz) and the power in the high frequency (HF) band (e.g., 0.15 to 0.4 Hz) of the time series defined by r1, r2, . . . , rQ generated based on the output signals.

Figure 4:
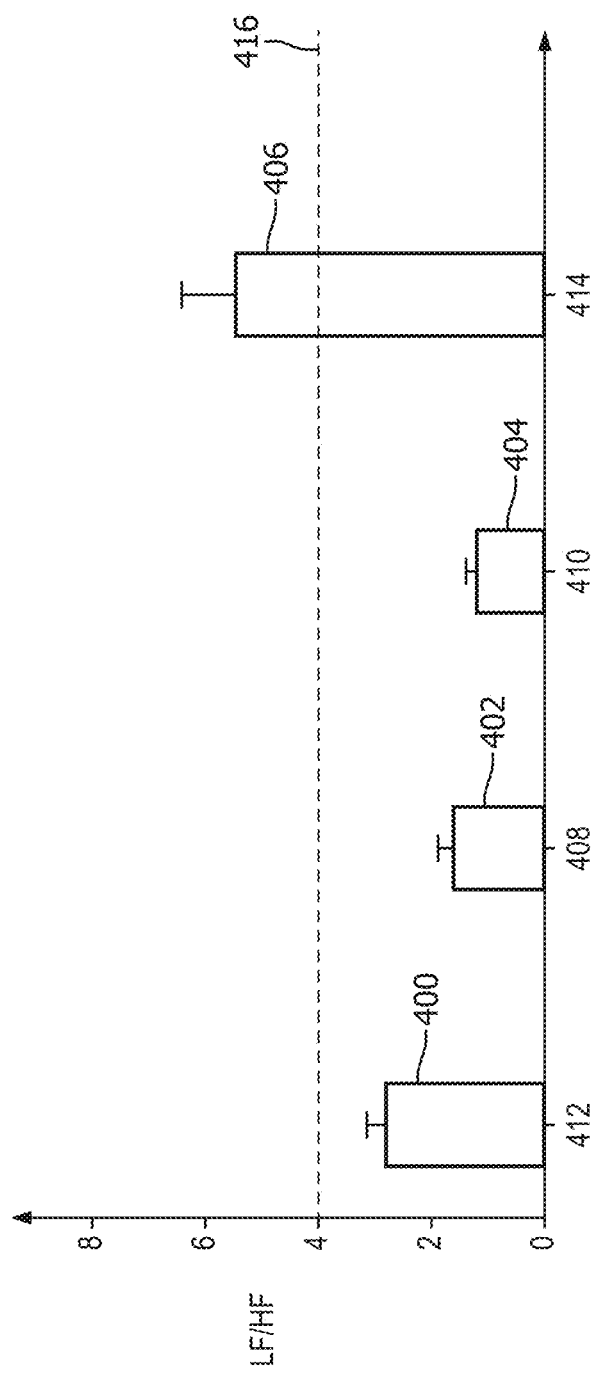
FIG. 4 illustrates a threshold on a ratio of a low frequency component of a cardiac activity signal to a high frequency component of the cardiac activity signal that may be used by the system to detect REM sleep and differentiate REM sleep from NREM sleep or wakefulness, in accordance with one or more embodiments.

Ratios (LF/HF) 400, 402, 404, and 406 for NREM sleep stages 408 and 410, wakefulness 412, and REM 414 are shown in FIG. 4. As shown in FIG. 4, a threshold 416 (e.g., of about 4) on the LF/HF ratio may be used by model component 32 (FIG. 1) to detect REM sleep and differentiate REM sleep from NREM sleep or wakefulness. In some embodiments, model component 32 is configured to determine the LF/HF ratio in real-time or near real-time. It should be noted that heart-rate variability can also be quantified as standard deviation of the RR-interval, i.e. the square root of the variance of r1, . . . , rQ. For instance, let $<r>$ be the average value of the sequence: r1, . . . rQ and $<r^2>$ be the average value of the sequence $r1^2$, . . . , $rQ^2$. Then the standard deviation is: $\sigma = \text{sqrt}(<r>\times<r>-<r^2>)$.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via user interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensor 14, sensory stimulator 16, external resources 18, processor 20, and/or other components of system 10. For example, a hypnogram, EEG data, REM sleep stage probability, and/or other information may be displayed for subject 12 or other users via user interface 24. As another example, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
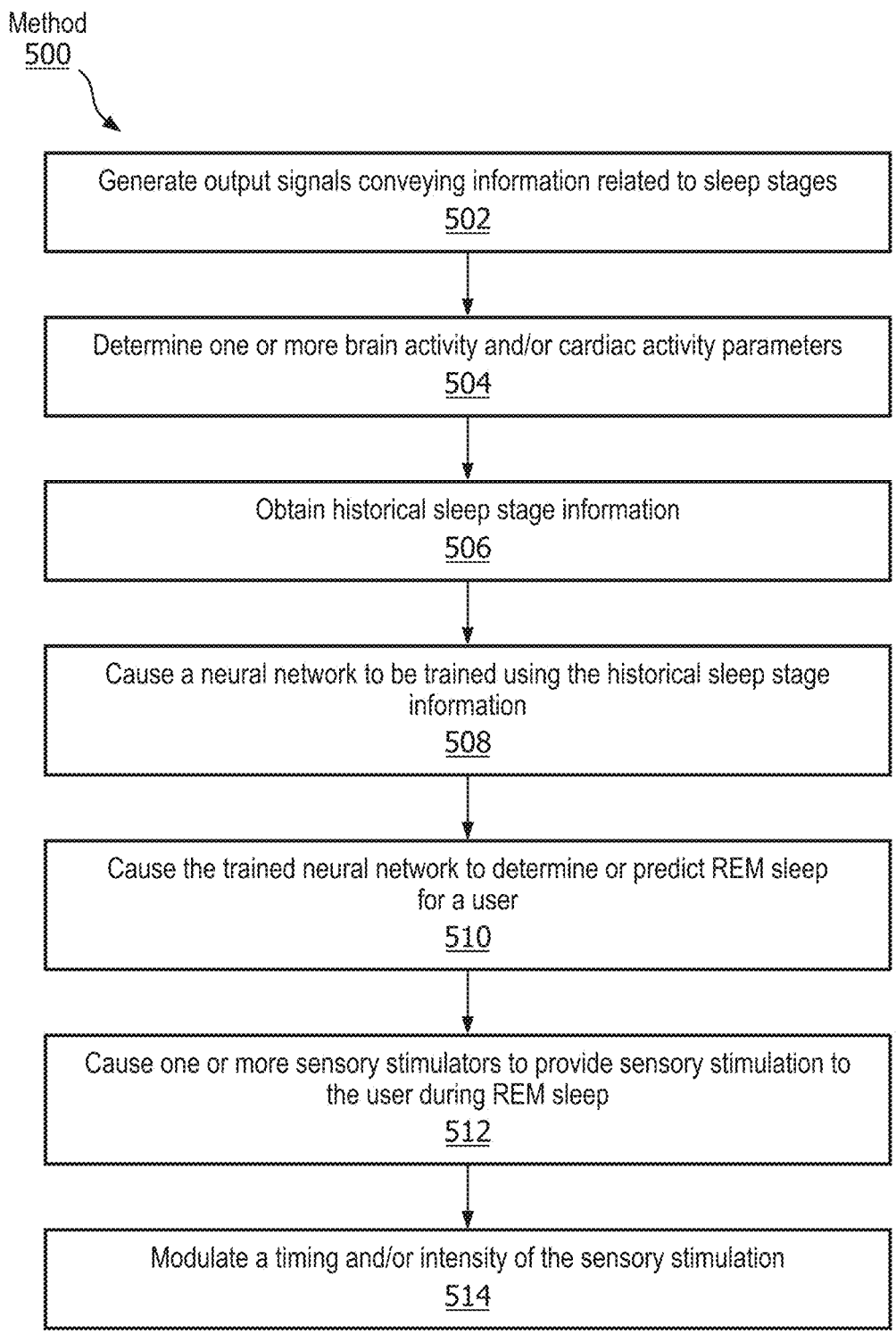
FIG. 5 illustrates method for enhancing REM sleep by delivering sensory stimulation to a subject during a sleep session with an enhancement system, in accordance with one or more embodiments.

FIG. 5 illustrates method 500 for enhancing REM sleep by delivering sensory stimulation to a subject during a sleep session with an enhancement system. The system comprises one or more sensors, one or more sensory stimulators, one or more hardware processors configured by machine-readable instructions, and/or other components. The one or more hardware processors are configured to execute computer program components. The computer program components comprise an information component, a model component, a control component, a modulation component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals conveying information related to sleep stages of the subject during the sleep session are generated. The output signals are generated during a sleep session of the user and/or at other times. In some embodiments, operation 502 is performed by sensors the same as or similar to sensors 14 (shown in FIG. 1 and described herein).

At an operation 504, one or more brain activity and/or cardiac activity parameters are determined. The information related to the sleep stages of the subject comprises information related to brain activity and/or cardiac activity in the subject. The brain activity and/or cardiac activity parameters are determined based on the output signals and/or other information. The brain activity and/or cardiac activity parameters indicate depth of sleep in the user. In some embodiments, operation 504 is performed by a processor component the same as or similar to information component 30 (shown in FIG. 1 and described herein).

At an operation 506, historical sleep stage information is obtained. The historical sleep stage information is for the subject and/or a population of subjects demographically similar to the subject. The historical sleep stage information is related to brain activity and/or cardiac activity of the subject and/or the population of subjects that indicates sleep stage over time during sleep sessions of the subject and/or the population of subjects. In some embodiments, operation 508 is performed by a processor component the same as or similar to information component 30 (shown in FIG. 1 and described herein).

At an operation 508, a neural network is trained using the historical sleep stage information. The neural network is trained based on the historical sleep stage information by providing the historical sleep stage information as input to the neural network. In some embodiments, training the neural network comprises causing the neural network to be trained. In some embodiments, operation 508 is performed by a processor component the same as or similar to model component 32 (shown in FIG. 1 and described herein).

At an operation 510, the trained neural network is caused to (1) determine periods when the subject is experiencing REM sleep during the sleep session; or (2) predict future times during the sleep session at which the subject will experience REM sleep. The trained neural network is caused to indicate REM sleep in the subject and/or future times at which the subject will be in REM sleep based on the output signals and/or other information. The trained neural network comprises one or more intermediate layers. The one or more intermediate layers of the trained neural network include one or more convolutional layers and one or more recurrent layers of the trained neural network.

In some embodiments, operation 510 includes providing the information in the output signals to the neural network in temporal sets that correspond to individual periods of time during the sleep session. In some embodiments, operation 510 includes causing the trained neural network to output the detected REM sleep and/or the future times of predicted REM sleep for the subject during the sleep session based on the temporal sets of information. In some embodiments, operation 510 is performed by a processor component the same as or similar to model component 32 (shown in FIG. 1 and described herein).

In some embodiments, operations 506-510 are replaced by detecting REM sleep in the subject based on the cardiac activity parameters (e.g., without using the trained neural network). In these embodiments, REM sleep in the subject is detected responsive to a ratio between a low frequency component of the information related to cardiac activity (e.g., a low frequency cardiac activity parameter) and a high frequency component of the information related to cardiac activity (e.g., a high frequency cardiac activity parameter) breaching a ratio threshold. In some embodiments, these operations are performed by a processor component the same as or similar to model component 32 (shown in FIG. 1 and described herein).

At an operation 512, the one or more sensory stimulators are caused to provide sensory stimulation to the subject during REM sleep to enhance the REM sleep. The one or more sensory stimulators are caused to provide the sensory stimulation based on the determinations of REM sleep in the subject and/or the predicted timing of REM sleep during the sleep session and/or other information. The one or more sensory stimulators are caused to provide the sensory stimulation to the subject responsive to a determination that the subject is in REM sleep and/or the future times indicating the subject will be in REM sleep for stimulation. In some embodiments, operation 512 is performed by a processor component the same as or similar to control component 34 (shown in FIG. 1 and described herein).

At an operation 514, the one or more sensory stimulators are caused to modulate an amount, a timing, and/or an intensity of the sensory stimulation based on the one or more brain activity and/or cardiac activity parameters and values output from the one or more intermediate layers of the trained neural network. The one or more sensory stimulators are caused to modulate the amount, timing, and/or intensity of the sensory stimulation based on the one or more brain activity parameters, one or more cardiac activity parameters, value output from the one or more convolutional layers, and/or values output from the one or more recurrent layers of the trained neural network.

In some embodiments, the sensory stimulation comprises audible tones. Causing the one or more sensory stimulators to modulate the timing and/or intensity of the sensory stimulation comprises adjusting an inter tone interval and/or adjusting a tone volume responsive to detection of REM sleep. In some embodiments, the stimulation is timed to synchronize to the detection of a PGO wave in the EEG. In some embodiments, operation 514 is performed by a processor component the same as or similar to modulation component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to enhance rapid eye movement (REM) sleep by delivering auditory stimulation to a subject during a sleep session, the system comprising:
   one or more sensors configured to generate output signals conveying information related to sleep stages of the subject during the sleep session;
   one or more sensory stimulators configured to provide the auditory stimulation to the subject during the sleep session; and
   one or more hardware processors coupled to the one or more sensors and the one or more sensory stimulators, the one or more hardware processors configured by machine-readable instructions to:
      detect REM sleep in the subject during the sleep session based on the output signals, and
      control the one or more sensory stimulators to provide the auditory stimulation to the subject during the REM sleep to enhance the REM sleep in the subject during the sleep session,
   wherein the one or more hardware processors are configured such that detecting the REM sleep in the subject comprises:
      obtaining historical sleep stage information for the subject and/or a population of subjects demographically similar to the subject, the historical sleep stage information being related to brain activity and/or cardiac activity of the subject and/or the population of subjects that indicates sleep stages over time during sleep sessions of the subject and/or the population of subjects;

causing a neural network to be trained based on the historical sleep stage information by providing the historical sleep stage information as input to the neural network; and causing, based on the output signals, the trained neural network to:
(1) determine periods when the subject is experiencing the REM sleep during the sleep session; or
(2) predict future times during the sleep session at which the subject will experience the REM sleep;
the trained neural network comprising an input layer, an output layer, and one or more intermediate layers between the input layer and the output layer.

2. The system of claim 1, wherein the one or more sensors are configured such that the information related to the sleep stages of the subject comprises information related to brain activity and/or cardiac activity in the subject.

3. The system of claim 2, wherein the one or more sensors comprise one or more electroencephalogram (EEG) electrodes configured to generate the information related to the brain activity, one or more electrocardiogram (ECG) sensors configured to generate the information related to the cardiac activity, and/or one or more photoplethysmography (PPG) sensors configured to generate the information related to the cardiac activity.

4. The system of claim 2, wherein the one or more sensors are configured such that the information related to the sleep stages of the subject comprises the information related to the cardiac activity, and wherein the one or more hardware processors are configured to detect the REM sleep in the subject responsive to a ratio between a low frequency component of the information related to the cardiac activity and a high frequency component of the information related to the cardiac activity breaching a ratio threshold.

5. The system of claim 1, wherein the one or more hardware processors are further configured to detect the REM sleep in the subject responsive to determining that the subject has remained in the REM sleep for a continuous threshold amount of time during the sleep session.

6. The system of claim 1, wherein the one or more hardware processors are configured such that controlling the one or more sensory stimulators to provide the auditory stimulation to the subject during the REM sleep to enhance the REM sleep in the subject during the sleep session comprises:
determining, with respect to (1) the periods when the subject is experiencing the REM sleep, or (2) each of the future times, one or more values generated by the one or more intermediate layers of the trained neural network;
causing the one or more sensory stimulators to provide the auditory stimulation to the subject (1) during the periods when the subject is experiencing the REM sleep, or (2) at the future times, and
determining, and/or causing the one or more sensory stimulators to modulate, an amount, a timing, and/or an intensity of the auditory stimulation provided to the subject based on the one or more values of the one or more intermediate layers.

7. The system of claim 6, wherein the one or more hardware processors are further configured to determine one or more brain activity and/or cardiac activity parameters of the subject based on the output signals, the one or more brain activity and/or cardiac activity parameters indicative of the sleep stages of the subject; and
determine, and/or cause the one or more sensory stimulators to modulate, the amount, timing, and/or intensity of the auditory stimulation to enhance the REM sleep in the subject based on the one or more values of the one or more intermediate layers and the one or more brain activity and/or cardiac activity parameters.

8. The system of claim 7, wherein the one or more hardware processors are configured such that the one or more values from the one or more intermediate layers of the trained neural network include values from one or more convolutional layers and values from one or more recurrent layers of the trained neural network, and to determine, and/or cause the one or more sensory stimulators to modulate, the amount, timing, and/or intensity of the auditory stimulation based on the one or more brain activity and/or cardiac activity parameters, the values from the one or more convolutional layers, and the values from the one or more recurrent layers.

9. The system of claim 1, wherein the one or more sensory stimulators are configured such that the auditory stimulation comprises audible tones, and
wherein the one or more hardware processors are configured such that controlling the one or more sensory stimulators to provide the auditory stimulation to the subject during the REM sleep to enhance the REM sleep in the subject during the sleep session comprises:
determining the amount, timing, and/or intensity of the auditory stimulation by determining an inter tone interval, a tone volume, and/or a tone frequency; and/or
causing the one or more sensory stimulators to modulate the amount, timing, and/or intensity of the auditory stimulation, the modulation comprising adjusting the inter tone interval, the tone volume, and/or the tone frequency, responsive to an indication the subject is experiencing one or more micro-arousals.

10. A method for enhancing rapid eye movement (REM) sleep by delivering auditory stimulation to a subject during a sleep session with an enhancement system, the system comprising one or more sensors, one or more sensory stimulators, and one or more hardware processors, the method comprising:
generating, with the one or more sensors, output signals conveying information related to sleep stages of the subject during the sleep session;
detecting, with the one or more hardware processors, REM sleep in the subject during the sleep session based on the output signals, and
controlling, with the one or more hardware processors, the one or more sensory stimulators to provide the auditory stimulation to the subject during the REM sleep to enhance the REM sleep in the subject during the sleep session,
wherein detecting the REM sleep in the subject comprises:
obtaining historical sleep stage information for the subject and/or a population of subjects demographically similar to the subject, the historical sleep stage information being related to brain activity and/or cardiac activity of the subject and/or the population of subjects that indicates sleep stages over time during sleep sessions of the subject and/or the population of subjects;
causing a neural network to be trained based on the historical sleep stage information by providing the historical sleep stage information as input to the neural network, the trained neural network comprising an input layer, an output layer, and one or more intermediate layers between the input layer and the output layer; and causing, based on the output signals, the trained neural network to:
(1) determine periods when the subject is experiencing the REM sleep during the sleep session; or
(2) predict future times during the sleep session at which the subject will experience the REM sleep; and wherein controlling the one or more sensory stimulators to provide the auditory stimulation to the subject during the REM sleep to enhance the REM sleep in the subject during the sleep session comprises:
determining, with respect to (1) the periods when the subject is experiencing the REM sleep, or (2) each of the future times, one or more values generated by the one or more intermediate layers of the trained neural network;
causing the one or more sensory stimulators to provide the auditory stimulation to the subject (1) during the periods when the subject is experiencing the REM sleep, or (2) at the future times; and
determining, and/or causing the one or more sensory stimulators to modulate, an amount, a timing, and/or an intensity of the auditory stimulation provided to the subject based on the one or more values of the one or more intermediate layers.

11. The method of claim 10, wherein the information related to the sleep stages of the subject comprises information related to brain activity and/or cardiac activity in the subject.

12. The method of claim 11, wherein the information related to the sleep stages of the subject comprises the information related to the cardiac activity, and wherein the one or more hardware processors are configured to detect the REM sleep in the subject responsive to a ratio between a low frequency component of the information related to the cardiac activity and a high frequency component of the information related to the cardiac activity breaching a ratio threshold.

13. The method of claim 10, further comprising determining, with the one or more hardware processors, one or more brain activity and/or cardiac activity parameters of the subject based on the output signals, the one or more brain activity and/or cardiac activity parameters indicative of the sleep stages of the subject; and
determining, and/or cause the one or more sensory stimulators to modulate, with the one or more hardware processors, the amount, timing, and/or intensity of the auditory stimulation to enhance the REM sleep in the subject based on the one or more values of the one or more intermediate layers and the one or more brain activity and/or cardiac activity parameters.

* * * * *